United States Patent
Hanes et al.

(10) Patent No.: US 8,354,476 B2
(45) Date of Patent: Jan. 15, 2013

(54) FUNCTIONALIZED POLY(ETHER-ANHYDRIDE) BLOCK COPOLYMERS

(75) Inventors: Justin Hanes, Baltimore, MD (US); Jie Fu, Baltimore, MD (US)

(73) Assignee: Kala Pharmaceuticals, Inc., Waltham, MA (US)

( * ) Notice: Subject to any disclaimer, the term of this patent is extended or adjusted under 35 U.S.C. 154(b) by 739 days.

(21) Appl. No.: 11/721,123

(22) PCT Filed: Dec. 9, 2005

(86) PCT No.: PCT/US2005/044658
§ 371 (c)(1),
(2), (4) Date: Sep. 21, 2009

(87) PCT Pub. No.: WO2006/063249
PCT Pub. Date: Jun. 15, 2006

(65) Prior Publication Data
US 2010/0003337 A1    Jan. 7, 2010

Related U.S. Application Data

(60) Provisional application No. 60/635,280, filed on Dec. 10, 2004.

(51) Int. Cl.
*C08G 63/91* (2006.01)
*C08G 67/04* (2006.01)
*C08G 67/00* (2006.01)
*C08G 63/00* (2006.01)

(52) U.S. Cl. ...... 525/419; 525/88; 525/92 F; 525/327.4; 525/430; 528/272; 528/297; 528/486

(58) Field of Classification Search .................. 525/419, 525/88, 92 F, 327.4, 430; 528/272, 297, 528/486
See application file for complete search history.

(56) References Cited

U.S. PATENT DOCUMENTS
2003/0086895 A1   5/2003 Hanes et al.

OTHER PUBLICATIONS

Fiegel, Jennifer, et al.; Poly(Ether-Anhydride) Dry Powder Aerosols for Sustained Drug Delivery in the Lungs; Journal of Controlled Release; 96 (2004) 411-423.
Fu, Jie, et al.; Synthesis and Characterization of PEG-Based Ether-Anhydride Terpolymers: Novel Polymers for Controlled Drug Delivery; Macromolecules 2004,37, 7174-7180; Department of Chemical and Bimolecular Engineering. The John Hopkins University.
Sakhalkar, Harshad S., et al.; Leukocyte-Inspired Biodegradable Particles That Selectively and Avidly Adhere to Inflamed Endothelium in Vitro and in Vivo; PNAS, Dec. 23, 2003, vol. 100, No. 26, 15895-15900.

*Primary Examiner* — Duc Truong
(74) *Attorney, Agent, or Firm* — Wolf, Greenfield & Sacks, P.C.

(57) ABSTRACT

The present application is directed to biodegradable polymers, compositions, including microspheres and nanospheres, formed of such polymers, and methods of using such polymers and compositions. In certain embodiments, the subject polymer compositions include therapeutic agents, optionally providing sustained release of the encapsulated agent after administration to a patient.

26 Claims, 4 Drawing Sheets

FUNCTIONALIZED POLY(ETHER-ANHYDRIDE) BLOCK COPOLYMERS

CROSS-REFERENCE TO RELATED APPLICATIONS

This application is a U.S. National Stage filing under 35 U.S.C. § 371 of International Application No. PCT/US2005/044658, filed Dec. 9, 2005, which claims the benefit under 35 U.S.C. § 119(e) of U.S. Provisional Application Ser. No. 60/635,280, filed Dec. 10, 2004, each of which is incorporated by reference herein in its entirety.

BACKGROUND OF THE INVENTION

Recently, there has been a revolution in biotechnology that is producing an abundance of potent new protein, peptide, and DNA-based drugs. Efficient, convenient, and effective means of delivering such therapeutics, however, are still needed.

Biodegradable polymers have been used for many applications in medicine, including controlled release drug delivery systems, resorbable bone pins and screws, and scaffolds for cells in tissue engineering. Systems based on biodegradable polymers obviate the need for surgical removal since their degradation products are absorbed or metabolized by the body. Micro- and nano-sized systems made using polymers can be used to deliver precise amounts of drugs, including small molecules, proteins and genes, over prolonged periods to local tissues or the systemic circulation. Of particular interest is the development of drug delivery vehicles that exhibit reduced detection rates by the immune system (e.g., long-circulating carriers for intravenous administration), or that can be administered via non-invasive delivery routes (such as inhalation). Biodegradable polymers that safely erode in the body, preferably at a rate that closely coincides with the rate of drug delivery, are required for these advanced applications.

Despite their wide and growing need in medicine, few synthetic biodegradable polymers are currently used routinely in humans, especially the ester copolymers of lactide and glycolide (PLGA family), and anhydride copolymers of sebacic acid (SA) and 1,3-bis(carboxyphenoxy)-propane (CPP). PLGA is the most widely used due to its history of safe use as surgical sutures and in current drug delivery products like the Lupron Depot. While the development of PLGA remains among the most important advances in medical biomaterials, there are some limitations that significantly curtail its use. First, PLGA particles typically take a few weeks to several months to completely degrade in the body, but the device is typically depleted of drug more rapidly. Repeated dosing of such a system leads to an unwanted build up of drug-depleted polymer in the body. This may preclude the use of PLGA for many applications, especially those that require injection of polymer drug carriers into the blood or, alternatively, their inhalation into the lungs. A second limitation is that PLGA devices undergo bulk-erosion, which leads to a variety of undesirable outcomes including exposure of unreleased drug to a highly acidic environment. Third, it is difficult to release drugs in a continuous manner from PLGA particles owing the polymers' bulk-erosion mechanism. Instead, special preparation methods are required with PLGA to avoid the typical intermittent drug release pattern (i.e., burst of drug followed by a period of little or no drug release, and then by the onset of a second phase of significant drug release). Fourth, the particularly fine PLGA particles needed for intravenous injection or inhalation can agglomerate significantly, making resuspension for injection or aerosolization for inhalation difficult. Finally, small, insoluble particles with hydrophobic surfaces, like those made with PLGA, are rapidly removed and destroyed by the immune system (due to fast opsonization).

Implants composed of poly(CPP:SA) were approved for use in humans in the 1990's to deliver chemotherapeutic molecules directly at the site of a resected brain tumor. CPP:SA copolymers erode from the surface-in (called surface-erosion), leading to desirable steady drug delivery rates over time. Proven biocompatibility, current clinical use, and steady drug release profiles make polymers composed of CPP and SA good candidates for new drug delivery applications. However, like PLGA particles, small particles made with poly(CPP:SA) possess hydrophobic surfaces that lead to rapid removal by the immune system and poor resuspension and aerosolization properties.

Hanes et al in USPA 2003/0086895 describes random copolymers of polyethylene glycols (PEG), sebacic acid, and, optionally, 1,3-bis(carboxyphenoxy)propane. These random copolymers have numerous medical uses (e.g., biodegradable drug delivery). However, due to the random incorporation of PEG into the copolymer, there is no free end of the PEG available for further manipulation. Such a free end would allow one of ordinary skill in the art to attach groups with desirable activities (e.g., targeting ligands or anti cancer drugs).

SUMMARY OF THE INVENTION

The present invention provides novel functionalized poly (ether-anhydride) block copolymers, wherein one end of the copolymer is capable of being attached to a moiety with a desirable characteristic (e.g., a targeting ligand, a drug, a monoclonal antibody, etc.).

The present invention also provides novel methods of using the copolymers of the present invention (e.g., therapy, diagnosing, imaging, and as an adjuvant).

The present invention also provides novel particles (e.g., microspheres and nanospheres) formed from the copolymers of the present invention. These particles may be used to encapsulate biologically active agents and deliver it to a patient in need thereof.

The present invention also provides novel compositions (e.g., pharmaceutical compositions) comprising the copolymers of the present invention.

The present invention also provides novel methods of making the copolymers of the present invention.

These and other features of the present invention, which will become apparent during the following detailed description, have been achieved by the inventors' discovery that block copolymers of polyethylene glycol can be formed by copolymerization with a functionalized PEG prepolymer.

DETAILED DESCRIPTION OF THE INVENTION

The present invention provides poly(ether-anhydride) block copolymers, which can be suitable for administration of therapeutic and biologically active agents, including sustained release administration, through a wide variety of routes, including microspheres and nanospheres for injection or inhalation. The polymers can be prepared using clinically approved monomers, including sebacic acid (SA), 1,3-bis (carboxyphenoxy)propane (CPP), and functionalized blocks of poly(ethylene glycol) (PEG) of various molecular weights. By controlling the composition of the present block copolymers, the properties of drug-loaded particles made from these new polymers can be optimized. These properties can provide a great deal of flexibility for the delivery of a wide range of drugs.

The present invention provides novel poly(ether-anhydride) block copolymers, comprising: subunits of a diacid and a subunit of Formula B:

B wherein:

Z is an end group that does not polymerize with the diacid; and, n is, independently for each occurrence, an integer from (a) 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, to 10,000 (b) 10 to 5,000; and, (c) 200 to 6,000.

The starting material or prepolymer of the subunit of Formula B is formed from a polyethylene glycol (e.g., PEG) of various molecular weights. One end of the PEG is functionalized with group Z, which is an end group that does not polymerize with the diacid. Z is a group that allows for attachment of a group having a desirable property (e.g., a peptide, protein, antigen, antibody, enzyme, nucleic acid, lectin, or any type of targeting or drug moiety). Z can allow for attached by itself being modifiable, by being partly or fully cleavable to expose a chemical group (e.g., an OH group) that is capable of being functionalized. By modifying the Z group to include a chemical moiety having a desirable property, the block copolymers of the present invention can be used for therapies that benefit from some type of targeting. These uses include, but are not limited to, targeted drug delivery, target gene/oligonucleotide delivery, vaccine delivery, medical imaging, diagnostics, and tissue engineering.

An example of a well known and useful Z group is Biotin, which can be attached to an α-hydroxy-ω-amine PEG via known chemistry to form a biotinamide Z group. This biotinamide can then be attached to a variety of groups via an avidin-biotin ligating procedure. For example, the biotin-PEG polymer can be reacted with neutravidin, and the resulting product can then be reacted with any biotinylated moiety.

Z also can be one of many other groups known to those of skill in the art, including OH, $NH_2$, COOH, and SH, which can be protected first with a known protecting group (see, for example, Greene and Wuts, *Protective Groups In Organic Synthesis*, Wiley and Sons, 1991), then deprotected after polymerization for further modification as discussed herein (e.g., attachment of a drug, peptide, or target compound, such as folic acid). The protecting group selected is one that does not polymerize with the other monomers that form the block copolymer. Typical examples of protecting groups are provided below. As will all examples provided herein, they should not be considered limiting. Examples of hydroxyl protecting groups include tetrahydropyranyl (THP), methoxymethyl (MOM), β-methoxyethoxymethyl (MEM), methylthiomethyl, t-butyl, triphenylmethyl (trityl), benzyl, allyl, silyl ethers (e.g., trimethylsilyl ether and t-butyldimethylsilyl ether), mesylate, tosylate, acetate, benzoate, N-acylimidazoles, and trichloroethyl chloroformate. Examples of amino protecting groups include carbobenzyloxy, t-butoxycarbonyl, phthaloyl, trichloroacetamide, and trifluoroacetyl. Examples of carboxylic acid protecting groups include esters (e.g., t-butyl ester and benzyl ester) and 2-oxazolines (from 2-amino-2-methyl-1-propanol or 2,2-dimethylaziridine).

Diacids are known to those of skill in the art. They correspond to a chemical moiety that is terminated by two carboxylic acids (i.e., $CO_2H$) or a derivative thereof (e.g., ester, anhydride, acid halide, etc.). The two carboxylic acids or derivatives thereof are separated by at least four aliphatic carbons (e.g., $(CH_2)_4$), at least four aromatic carbon atoms (e.g., a 1,4-disubstituted benzene), or a combination thereof (e.g., $(CH_2)_{4\text{-}20}$, $(CH_2)_{1\text{-}20}$-phenyl-$(CH_2)_{1\text{-}20}$). The aliphatic or aromatic carbon atoms can be substituted by 1-6 groups including, but not limited to, $C_{1\text{-}6}$ alkyl, benzyl, phenyl, F, Cl, Br, I, $CF_3$, and $NO_2$, as long as the substituent does not prohibit polymerization between the diacid and the subunit of Formula B. Examples of diacids include, but are not limited to, hexanedioic acid (adipic acid), heptanedioic acid (pimelic acid), octanedioic acid (suberic acid), nonanedioic acid (azelaic acid), decanedioic acid (sebacic acid), undecanedioic acid, dodecanedioic acid, 1,1-undecanedicarboxylic acid, 1,12-dodecanedicarboxylic acid, 1,3-bis(carboxyphenoxy) propane (CPP), 1,3-bis(carboxyphenoxy)hexane (CPH), isophthalic acid (1,3-phenyl dicarboxylic acid), terephthalic acid (1,4-phenyl-dicarboxylic acid), diphenic acid (2,2'-biphenyl dicarboxylic acid), 3,3'-dimethyl-biphenyl-2,2'-dicarboxylic acid, biphenyl-4,4'-dicarboxylic acid and, 1,2-cyclohexanedicarboxylic acid.

In another embodiment, the diacid forms a subunit of formula A:

A wherein:

m is, independently for each occurrence, an integer from (a) 4, 5, 6, 7, 8, 9, 10, 11, 12, 13, 14, 15, 16, 17, 18, 19, to 20; (b) 4-12; and, (c) 8;

p is, independently for each occurrence, an integer from (a) $\geq 1$, (b) 5, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, to 10,000 (c) 1-5,000, (d) 5-10,000, and (e) 10-5,000.

In another embodiment, the block copolymer further comprises subunits of formula C:

C wherein:

r is, independently for each occurrence, an integer from (a) $\geq 1$, (b) 5, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, to 10,000 (c) 1-5,000, (d) 5-10,000, and (e) 10-5,000; and, q is, independently for each occurrence, an integer from (a) 1, 2, 3, 4, 5, 6, 7, 8, 9, 10, 11, 12, 13, 14, 15, 16, 17, 18, 19, to 20; (b) 2 to 10; (c) 2 to 6; and, (d) 3 or 6.

It is noted that the block copolymers of the present invention are terminated on one end by Z and on the other end by the free end of the diacid or Formula C, if present. The non-Z end of the copolymer can be the free acid, a group remaining from the prepolymer of the diacid or Formula C, or optionally a group resulting from the post-polymerization functionalization (e.g., a $C_{1-8}$ alkyl ester). Examples of prepolymer terminal groups include $C_{1-8}$ alkyl, $C_{1-8}$ alkylC(O)— (e.g., $CH_3C(O)$—), HOOC—R—C(O)—, amino alkyl groups (e.g., $H_2NCH_2CH_2$—), or any other group that allows reaction with the other prepolymers used to form the block copolymers of the present invention. The R group includes an aliphatic group (e.g., $C_{1-8}$ alkyl), aromatic groups (e.g., phenyl and bi-phenyl), or a mixture of aliphatic and aromatic groups.

The block copolymers of the present invention can be readily processed into nearly any shape or size and used like previously known medical polymers (e.g., implants, coatings on stents, etc.). The block copolymers of the present invention can also be formed into particles. Particles (e.g., biodegradable particles) made from block copolymers of the present invention possess a hydrophobic polymer core and hydrophilic PEG shell. This is due to the functionalized PEG moiety partitioning to the surface of the particle. As a result, the surface of the particles of the present invention can be easily modified. Modification of the present particles can produce particles that more readily cross biological barriers (e.g., they are less adhesive with mucus). In addition, molecules that are attached to the end of flexible PEG molecules, therefore, partition selectively to the surface of the particles upon formulation, thus making the attached molecules readily available to the body.

A wide variety of molecules (e.g., targeting ligands, peptides, proteins, antigens, antibodies, enzymes, nucleic acids, lectins, and drugs (e.g., anticancer and anti-inflammatory) can be attached to the functionalized end (i.e., non-polymerized end) of PEG under mild conditions to form poly(diacid acid-co-PEG-Ligand) micro- or nanospheres for biological applications, including targeted drug and gene delivery, medical imaging, diagnostics, and tissue engineering. Additional utilities include tissue or cell-specific and/or sustained delivery of chemotherapeutic agents for treatment of cancers (e.g., breast cancer, brain cancer, bone cancer, lung cancer, gastrointestinal, liver, prostate, pancreatic, cervical, bladder, vaginal, and colon cancer, etc.) and targeted drug delivery to inflamed endothelium for treatment of an array of pathologies, including cardiovascular disease, arthritis, inflammatory bowel disease, and cancer.

A desirable property of the present block copolymers is that they can be prepared such that they degrade at a rate that closely coincides with drug release times. Another favorable property of the present particles is that their size can be easily controlled (e.g., sizes ranging from 30 nm to over 100 µm are readily accessible).

In the copolymers of the present invention, m, n, and q each, independently, can be a constant value throughout the copolymer, i.e., m, n, and q do not vary within a subunit of Formula A, B, or C, or within different subunits of the same formula, within a sample of polymer or a polymer chain. The copolymers of the present invention may further comprise monomeric units other than those subunits represented by the diacid (e.g., Formula A) and Formula B and, optionally, the diacid of Formula C. In other embodiments, however, the polymer consists essentially of subunits of the diacid (e.g., Formula A), and Formula B and optionally Formula C.

The uncapped end of the present polymers may be capped (i.e., terminated) with H (to form carboxylic acids), acyl groups (to form anhydrides), alkoxy groups (to form esters), or any other suitable capping groups.

Examples of molecular weights for the subunits of Formula B include (a) 200, 300, 400, 500, 600, 700, 800, 900, 1,000, 10,000, 20,000, 30,000, 40,000, 50,000, 100,000, 200,000, 300,000, 400,000, 500,000, 600,000, 700,000, 800,000, 900,000 to 1,000,000 daltons, (b) 1000, 2000, 3000, 4000, 5000, 6000, 7000, 8000, 9000, up to 30000 daltons. The subunits of Formula B may have molecular weights that vary throughout the polymer (e.g., between 200 and 100,000 or more daltons). Alternatively, the subunits of Formula B may have molecular weights that vary only within a narrow range (e.g., 200-300 daltons or 2,000-3,000 daltons).

Examples of weight ranges for the diacid (e.g., subunit of Formula A) include (a) between 10-99% by weight of the polymer and (b) between 15-% by weight of the polymer. Examples of weight ranges for the subunit of Formula B include (a) between 1-90% by weight of the polymer and (b) between 2-60% by weight of the polymer.

When optional subunit C is present, examples of weight ranges for the diacid (e.g., subunit of Formula A) include between 10-98% by weight of the polymer. Examples of weight ranges for the subunit of Formula B include between 1-80% by weight of the polymer. Examples of weight ranges for the subunit of Formula C include between 1-95% by weight of the polymer.

The block copolymers of the present invention may have molecular weights ($M_w$) ranging from (a) about 2000 or less to about 300,000, 600,000 or 1,000,000 or more daltons, (b) at least about 10,000, 15,000, 20,000, 25,000, 30,000, 35,000, 40,000, 45,000, or 50,000 daltons, and (c) at least about 100,000 daltons. The block copolymers of the present invention may have number-average molecular weight ($M_n$) that may also vary widely, but generally fall in the ranges of (a) about 1,000 to about 200,000 daltons, (b) about 10,000 to about 100,000 daltons, (c) about 8,000 to about 50,000 daltons, and (d) about 12,000 and 45,000 daltons.

In another embodiment, the present invention provides novel compositions comprising the present block copolymers. A specific type of composition is a pharmaceutical composition, which can be for the delivery of biologically active agent, e.g., for the prevention or treatment of a disease or other condition in a patient. The pharmaceutical composition may further comprise a pharmaceutically acceptable carrier.

In another embodiment, the block copolymers of the present invention are formed into particles (e.g., microspheres or nanospheres). The micro- or nanospheres of the present invention maybe used for the sustained release of an encapsulated agent. Microparticles and microspheres are used interchangeably herein. Nanoparticles and nanospheres are used interchangeably herein. Microspheres and nanospheres can be formed by a wide variety of techniques known to those of skill in the art. Different methods can be employed to form micro- or nanospheres depending upon the desired application. Suitable methods include, but are not limited to, spray drying, solvent evaporation, emulsion methods, phase separation, freeze drying, air drying, vacuum drying, fluidized-bed drying, milling, co-precipitation and critical fluid extraction.

In another embodiment, the present invention provides novel compositions comprising one of the block copolymers and an encapsulated agent (e.g., therapeutic agent, diagnostic agent, imaging agent, and/or an adjuvant). Agents that may be encapsulated in the subject compositions include imaging and diagnostic agents (such as radiopaque agents, labeled antibodies, labeled nucleic acid probes, dyes, etc.), adjuvants (radiosensitizers, immunomodulatory molecules, transfection-enhancing agents (such as chloroquine and analogs thereof)), chemotactic agents and chemoattractants, peptides (e.g., peptides that modulate cell adhesion and/or cell mobility, cell permeabilizing agents, inhibitors of multidrug resistance and/or efflux pumps, etc.). The present invention also relates to methods of administering such compositions, e.g., as part of a treatment regimen, for example, by inhalation, or injection (e.g., subcutaneously, intramuscularly, or intravenously). As noted above, the block copolymer that encapsulates the agent can be in the form of a micro- or nanosphere.

The present pharmaceutical compositions, under biological conditions, e.g., upon contact with body fluids including blood, interstitial fluid, mucus, cell interiors, spinal fluid, lymph or the like, release the encapsulated drug over a sustained or extended period (as compared to the release from an isotonic saline solution). Such a system may result in prolonged delivery of effective amounts (e.g., 0.0001 mg/kg/hour to 10 mg/kg/hour) of the drug. Delivery times can include (a) 8, 16, 24, 48, 96, 120, 144, 168, 800, 1600, to 2400 or more hours or (b) 1, 2, 3, 4, 5, 6, 7, 8, 9, 10, to 100 or more days.

The block copolymers of the present invention may be used in the presence of a solvent to facilitate mixing or to maintain the flowability of the polymer composition. Examples of suitable biocompatible solvents include, but are not limited to, N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, oleic acid, and 1-dodecylazacycoheptanone.

Polymers of the present invention can be prepared by combining a mixture of compounds of a prepolymer of a diacid (e.g., Formula $A_1$) and Formula $B_1$ and optionally Formula $C_1$, depicted below, and heating at a temperature and for a time sufficient to form a polymer. For example, the mixture can be heated to a temperature sufficient to melt the prepolymers, for example (a) about 120, 130, 140, 150, 160, 170, 180, 190, to 200 or (b) about 140-190. The reaction can be run for (a) about 10, 15, 20, 25, 30, 35, 40, 45, 50, 55, 60, 70, 80, 90, 100, 200, 300, 400, 500, 600, 700, 800, 900, 100, to 1440 or more minutes or (b) about 20-180 minutes. When prepolymer $C_1$ is present, the mixture can be heated to a temperature of (a) about 120, 130, 140, 150, 160, 170, 180, 190, 200, 210, to 220 or (b) about 140-200. When prepolymer $C_1$ is present, the reaction can be run for (a) about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, 500, 600, 700, 800, 900, 100, to 1440 or more minutes. As understood by those of skill in the art, the reaction times and temperatures can be varied to achieve different molecular weight polymers.

$R^1$ is a group that is capable with reacting with the prepolymers of the diacid (e.g., Formula $A_1$), the prepolymer of the optional subunit of Formula C (e.g., Formula $C_1$), the prepolymer of any other subunit present, or a combination of these prepolymers. Examples a possible $R^1$ groups include H, $C_{1-8}$ alkylC(O)— (e.g., $CH_3C(O)$—), HOOC—R—C(O)—, amino alkyl groups (e.g., $H_2NCH_2CH_2$—), The R group includes an aliphatic group (e.g., $C_{1-8}$ alkyl), aromatic groups (e.g., phenyl and bi-phenyl), or a mixture of aliphatic and aromatic groups.

Y is a group that allows for prepolymers $A_1$ (i.e., the diacid prepolymer) and $C_1$, if present, to react with themselves, each other, and with the PEG prepolymer $B_1$. Examples of Y include H, $C_{1-8}$ alkyl (e.g., methyl), $OC_{1-8}$ alkyl, $SC_{1-8}$ alkyl, and $NHC_{1-8}$ alkyl. Also, Y, together with the $CO_2$ to which it is attached, may form a carbonate, carbamate, or ester moiety.

The polymerization may be conducted under vacuum, e.g., >1 Torr or >0.1 Torr). The polymerization may also be conducted in the presence of a solvent (e.g., an organic solvent). It can be desirable for the solvent to have a boiling point at a temperature above the reaction temperature, e.g., by at least 10° C., or even by at least 30° C. Examples of organic solvents include, but are not limited to, dimethylsulfoxide (DMSO) and sulfolane. A catalyst (e.g., Lewis acid catalyst) can be used. Examples of Lewis acid catalysts include, but are not limited to cadmium acetate and a lanthanide halide or alkoxide (e.g., samarium triisopropoxide).

Biologically active agent, as used herein, includes drug, therapeutic agent, medicament, or bioactive substance, which are biologically, physiologically, or pharmacologically active substances that act locally or systemically in the human or animal body. The term bioactive agent includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Alkyl, as used herein, refers to a saturated hydrocarbon chain having the specified number of carbon atoms (e.g., 1-8). An allyl chains may be straight (e.g., n-butyl) or branched (e.g., sec-butyl, isobutyl, or t-butyl). Alkyl groups may be unsubstituted or substituted with from 1 to 4 substituents selected from F, Cl, Br, I, haloalkyl (e.g., $CF_3$), hydroxy, and aryl (e.g., phenyl, tolyl, alkoxyphenyl, alkyloxycarbonylphenyl, halophenyl).

The particles of the present invention may have various coatings applied to modify their properties. Three exemplary types of coatings are seal, gloss and enteric coatings. Other types of coatings having various dissolution or erosion properties may be used to further modify subject matrices behavior, and such coatings are readily known to one of ordinary skill in the art. The seal coat may prevent excess moisture uptake by the matrices during the application of aqueous based enteric coatings. The gloss coat generally improves the handling of the finished matrices. Water-soluble materials such as hydroxypropylcellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as EUDRAGIT, RohmTech, Inc., Malden, Mass., and AQUATERIC, FMC Corp., Philadelphia, Pa., may be used and are layered as thin membranes onto the implants from aqueous solution or suspension or by a spray drying method. The enteric coat is generally sprayed to a weight increase of about one to about 30%, preferably about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

The present block copolymers can be useful as biodegradable delivery systems. In its simplest form, a biodegradable delivery system for a therapeutic agent consists of a dispersion of such a therapeutic agent in a polymer matrix. In other embodiments, an article is used for implantation, injection, or otherwise placed totally or partially within the body, the article comprising the present block copolymers. It is particularly desirable that such an article result in minimal tissue irritation when implanted or injected into vasculated tissue.

Dosages and Formulations

In most embodiments, the block copolymers will incorporate the substance to be delivered in an amount sufficient to deliver to a patient a therapeutically effective amount of an incorporated therapeutic agent or other material as part of a prophylactic or therapeutic treatment. The desired concentration of active compound in the particle will depend on absorption, inactivation, and excretion rates of the drug as well as the delivery rate of the compound from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The block copolymers of the present invention may be administered by various means, depending on their intended use, as is well known in the art. For example, if subject compositions are to be administered orally, it may be formulated as tablets, capsules, granules, powders or syrups. Alternatively, formulations of the present invention may be administered parenterally as injections (intravenous, intramuscular, or subcutaneous), drop infusion preparations, or suppositories. For application by the ophthalmic mucous membrane route, subject compositions may be formulated as eyedrops or eye ointments. These formulations may be prepared by conventional means, and, if desired, the subject compositions may be mixed with any conventional additive, such as a binder, a disintegrating agent, a lubricant, a corrigent, a solubilizing agent, a suspension aid, an emulsifying agent or a coating agent.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose vary depending upon the subject being treated, and the particular mode of administration.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated analgesic.

Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

When inhaled, the particle size of the particulate medicament should be such as to permit inhalation of as much of the medicament into the lungs as possible upon administration of the aerosol formulation and will thus desirably be less than 20 microns, preferably in the range 1 to 10 microns if inhaled as a dry powder, e.g., 1 to 5 microns. The particle size of the medicament may be reduced by conventional means, for example by milling or micronisation. The final aerosol formulation desirably contains 0.005-90% w/w, preferably 5-80% w/w, especially 5-50% w/w, of medicament relative to the total weight of the formulation.

Optionally, the aerosol formulations according to the invention may further comprise one or more surfactants, which include L-α-phosphatidylcholine (PC), 1,2-dipalmitoylphosphatidylcholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

The amount of surfactant employed in coating the particulate medicament is desirably in the range 0.1 to 10% w/w preferably 1 to 10% w/w, relative to the medicament Where the surfactant is present as a surface coating, the amount may advantageously be chosen such that a substantially monomolecular coating of sent is formed. However, it is preferable that the formulations of the invention are substantially free of surfactants, i.e., contain less than an effective stabilizing amount of a surfactant such as less than 0.0001% by weight of medicament.

The formulations of the invention may be prepared by dispersal of the medicament in a selected propellant and/or co-propellant in an appropriate container, e.g., with the aid of sonication. Preferably the particulate medicament is suspended in co-propellant and filled into, a suitable container. The valve of the container is then sealed into place and the propellant introduced by pressure filling through the valve in the conventional manner. The active ingredient may be thus suspended or dissolved in a liquified propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the microspheres (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the compound. Ordinarily, an aqueous aerosol is made by formulating an aqueous solution or suspension of the polymeric materials together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Ophthalmic formulations, eye ointments, powders, solutions and the like, are also contemplated as being within the scope of this invention.

Certain pharmaceutical compositions of this invention suitable for parenteral administration comprise one or more subject compositions in combination with one or more pharmaceutically acceptable sterile isotonic; aqueous or non-aqueous solutions, dispersions, suspensions or emulsions, or sterile powders which may be-reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Microsphere and/or nanosphere compositions may be suspended in a pharmaceutically acceptable solution, such as saline, Ringer's solution, dextran solution, dextrose solution, sorbitol solution, a solution containing polyvinyl alcohol (from about 1% to about 3%, preferably about 2%), or an osmotically balanced solution comprising a surfactant (such as Tween 80 or Tween 20) and a viscosity-enhancing agent (such as gelatin, alginate, sodium carboxymethylcellulose, etc.). In certain embodiments, the composition is administered subcutaneously. In other embodiments, the composition is administered intravenously. For intravenous delivery, the composition is preferably formulated as microspheres or nanospheres on average less than about 15 microns, more particularly less than about 10 microns, and still more particularly less than about 5 microns in average diameter.

The invention now being generally described, it will be more readily understood by reference to the following examples, which are included merely for purposes of illustration of certain aspects and embodiments of the present invention, and are not intended to limit the invention.

EXAMPLES

All chemicals were purchased from Sigma-Aldrich (St Louis, Mo.) unless otherwise noted. Sebacic acid was recrystallized three times from ethanol. Acetic anhydride was purified by distillation. Toluene and chloroform (J. T. Baker, Phillipsburg, N.J.) were refluxed over and distilled from calcium hydride. α-Hydroxy-ω-amine PEG was purchased from EKTAR. 1,3-bis(carboxyphenoxy)propane (CPP) was synthesized according to the method described by Conix (Macromol. Synth. 1966, 2, 95). Cadmium acetate, polyvinyl alcohol (88 mol % hydrolyzed, $M_w$=25 kDa, Polysciences Inc., Warrington, Pa.), bovine serum albumin (BSA), pyridine, 1,2-dipalmitoylphosphatidylcholine (DPPC), L-α-phosphatidylcholine (PC), succinic anhydride, and other reagents were used as received without further purification.

$^1$H NMR spectra were recorded in $CDCl_3$ on a Varian UNITY-400 MHz spectrometer, and FT-IR spectra were obtained by Perkin-Elmer 1600 series spectrometer (KBr pellet). The molecular weight of the polymer was determined by GPC analysis in chloroform (PU-980 intelligent HPLC pump, 1560 intelligent column thermoset, RI-1530 intelligent RI detector), with polystyrene as standards. (JASCO GPC). The microspheres were evaluated for surface morphology by scanning electronic microscopy (SEM) with an AMRAY 1860 FE microscope. Thermal analysis was performed using a SEKIO DSC220, where an average sample weight of 5-10 mg was heated at heating rates 10° C./min from −100° C. to 200° C.

Sebacic Acid (SA) Prepolymer

SA (10.0 g) was refluxed in 100 mL acetic anhydride under $N_2$ for 15 min and evaporated to dryness. The crude prepolymer was recrystallized from dried toluene, washed with anhydrous ethyl ether/petroleum ether (1:1), and finally dried by vacuum.

Biotin-PEG-OH Prepolymer

Biotin-PEG-OH was synthesized according to a procedure previously reported. α-Hydroxy-ω-amine PEG (1.0 g) was dissolved into acetonitrile (2 mL). Methylene chloride (1 mL) & pyridine (80 μl) were added and the mixture then stirred for 1 minute. After addition of NHS-Biotin (0.25 g), the reactants were stirred overnight under argon. The reaction was worked-up by the slow addition of diethyl ether (40 mL) to precipitate the polymer, which were then filtered on a Buchner funnel and washed with diethyl ether. The isolated material was then dissolved in hot isopropanol (70° C.). The polymer was reprecipitated on cooling. The polymer (350 mg) was dissolved into toluene (70 mL) and refluxed with a Dean-Stark trap and a condenser. 70% of the toluene was removed by distillation. The polymer was isolated on a rotary evaporator. To remove residual solvent, the polymer was dried under vacuum for 2 days. This product was then analysed for biotin attachment by $^1$H-NMR spectroscopy (see structure below and FIGS. 1 and 2).

Figure 1:
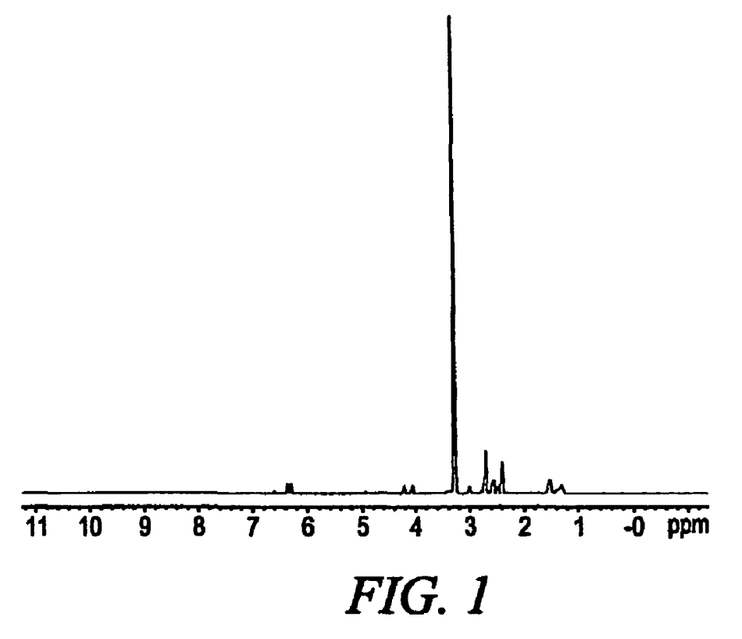
FIG. 1 presents the $^1$H NMR spectra of Biotin-NHS.
Figure 2:
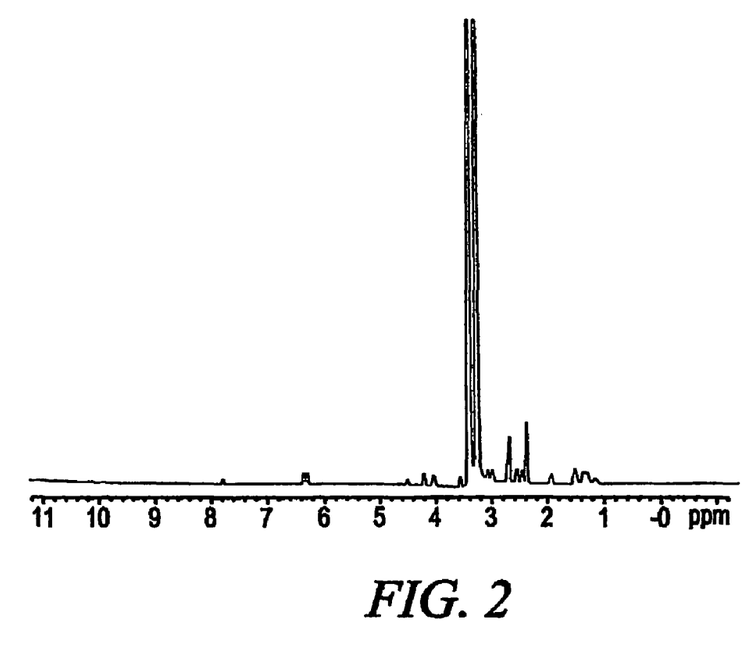
FIG. 2 presents the $^1$H NMR spectra of Biotin-PEG.

| H-a = 2.03 | H-e = 3.08 | H-i = 6.34 |
| H-b = 1.62 | H-f = 2.64, 2.57 | H-j = 6.40 |
| H-c = 1.47 | H-g = 4.28 | H-k = 7.81 |
| H-d = 1.27 | H-h = 4.11 | H-l = 3.49 |

$^1$H NMR spectra were recorded on a Varian UNITY-400 MHz spectrometer. The appearance of a triplet at 2.03 ppm that can be assigned to the methylene from the biotin chain "a" to the amide and the appearance of a broad singlet belonging to the free amido proton at 7.81 ppm. These signals were not present on the NMR of spectra of NHS-biotin. The biotin group was identified through the two methine protons (H-g, H-h) from the cyclic biotin structure at 4.28 and 4.12 ppm and two urea protons (H-j, H-i) from the cyclic biotin structure at 6.40, 6.34 ppm (ref. 5253). $^1$H NMR confirm the attachment of biotin to the PEG chain.

CPP Prepolymer

CPP (10.0 g) was refluxed in 200 mL acetic anhydride for 30 min under $N_2$, followed by removal of the unreacted diacid by filtration and evaporation to remove solvent. The residue was recrystallized from dimethylformamide (DMF) and ethyl ether, then washed with dry ethyl ether and dried under vacuum.

Biotin-PEG-PSA Polymer Synthesis

Biotin-PEG-PSA was prepared by melt polycondensation of Biotin-PEG-OH and SA prepolymer under high vacuum. The polymers were precipitated from chloroform into petroleum ether and dried by vacuum. The structure of PSA-PEG-biotin were confirmed by FT-IR and $^1$H NMR (see structure below and FIGS. 3 and 4).

Figure 3:
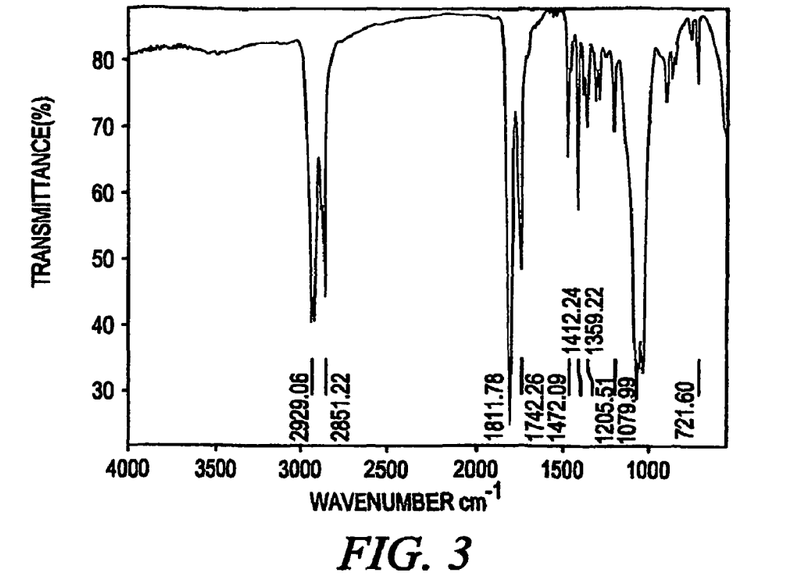
FIG. 3 presents the FT-IR spectra of Biotin-PEG-PSA (15:85).
Figure 4:
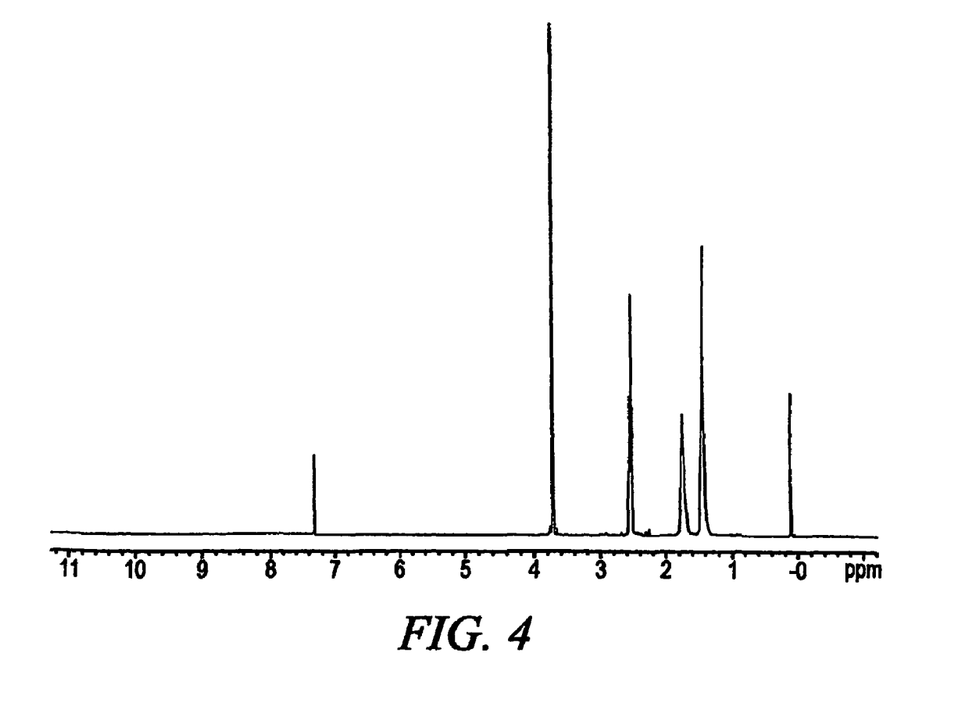
FIG. 4 presents the $^1$H NMR spectra of Biotin-PEG-PSA (15:85).

H-a = 2.44 H-b = 1.65 H-c = 1.33 H-d = 3.65

Figure 5:
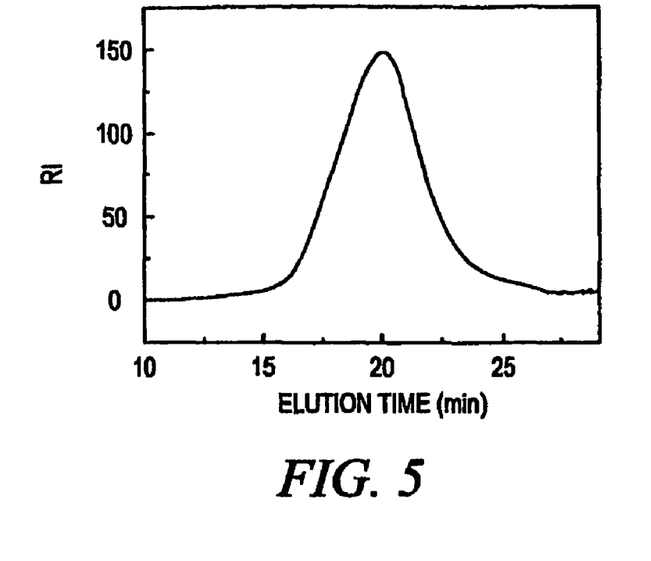
FIG. 5 presents the GPC chromatogram of Biotin-PEG-PSA.

The three peaks at 2.44, 1.65, and 1.33 ppm were attributed to the methylene protons of SA. The resonance line of the methylene protons of PEG appeared at 3.65 ppm, which indicated PEG was incorporated into polymer. The biotin signal was very weak due to the low amount of this compound in PSA-PEG-biotin. As the biotin moieties are attached to the PEG end group, the appearance of ethylene glycol unites in polymer suggests of biotin available in polymer. Infrared (IR) spectra were obtained using a Perkin-Elmer 1600 series spectrometer. The samples were ground and pressed into KBr pellets for analysis. The typical anhydride IR double peaks appeared at ~1812, ~1742 cm$^{-1}$, indicating efficient conversion of the SA to PSA. Gel permeation chromatography (GPC) measurement was carried out using a JASCO PU-980 intelligent HPLC pump, 1560 intelligent column thermoset, RI-1530 intelligent refractive index detector. Samples were filtered and eluded in chloroform through a series of Styragel columns (guard, HR4, and HR3 Waters Styragel columns) at a flow rate of 0.3 mL/min. The molecular weights were determined relative to polystyrene standards (Fluka, Milwaukee, Wis.). GPC revealed one peak (FIG. 5), indicative of pure polymer formed.

Preparation of Biotin-PEG-PSA Nanoparticles

Figure 7:
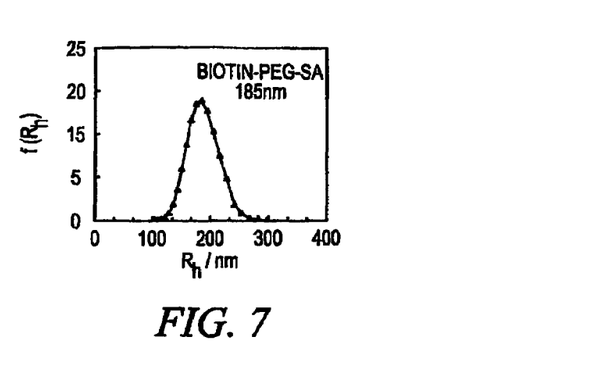
FIG. 7 presents the graph of the size distribution of nanoparticles of Biotin-PEG-PSA.

Nanospheres were prepared using a single emulsion solvent method. 50 mg of PSA-PEG-biotin (15:85) were dissolved in 5 mL of dichloromethane to produce a 25 mg/mL solution. PVA (250000 Mw) [88% hydrolyzed] was dissolved into distilled water to make a 0.1, and 5% w/v solution. The PSA-PEG-biotin solution was then added to 5% PVA, sonicated for 3 minutes, poured into 0.1% PVA and left stirring 3 hours for dichloromethane to evaporate. Particles were collected by centrifugation, washed in distilled water. Nanoparticle size (FIG. 7) analysis was performed Dynamic Light Scattering (DLS) using a Zetasizer® 3000 (Malvern Instruments Inc. Southborough, Mass.) with sample diluted in filtered distilled water. The measurements were performed at 25° C. at a scattering angle of 90°.

Characterization of PEG-SA

Biotin was attached to PEG through N-Hydroxy-succinimide chemistry. The Biotin-PEG with end group OH was then polymerized with the prepolymer of sebacic acid at high vacuum by melt-polycondensation to get PSA-PEG-Biotin (structure shown below) (see table 1).

TABLE 1

Characterization of PSA-PEG-Biotin

| Polymer[a] | PSA-PEG-biotin 95:5 | PSA-PEG-biotin 85:15 | PSA-PEG-biotin 75:25 |
|---|---|---|---|
| Yield (%) | 85 | 86 | 72 |
| PEG/SA (Feed) Wt. | 5:95 | 15:85 | 25:75 |
| [b]PEG/SA ($^1$H NMR) Wt. | 5.4:94.6 | 16.3:83.7 | 25.8:74.2 |
| [c]DP$_{PEG}$ | 77 | 77 | 77 |
| [d]DP$_{PSA}$ | 354 | 104 | 58 |
| M$_w$ (kDa) | 57.0 | 31.0 | 13.0 |
| M$_n$ (kDa) | 16.4 | 14.2 | 5.7 |
| PDI | 3.5 | 2.2 | 2.2 |

[a]polymers were polymerized at 160° C., 0.05-0.06 torr for 30 minutes.
[b]Estimated from integrat height of hydrogen shown in the $^1$H NMR spectra.
[c]DP$_{PEG}$ = (3400- 17)/44 = 77.
[d]DP$_{PSA}$ were calculated from $^1$H NMR.

Preparation of Biotin-PEG-PSA Microparticles

Figure 6:
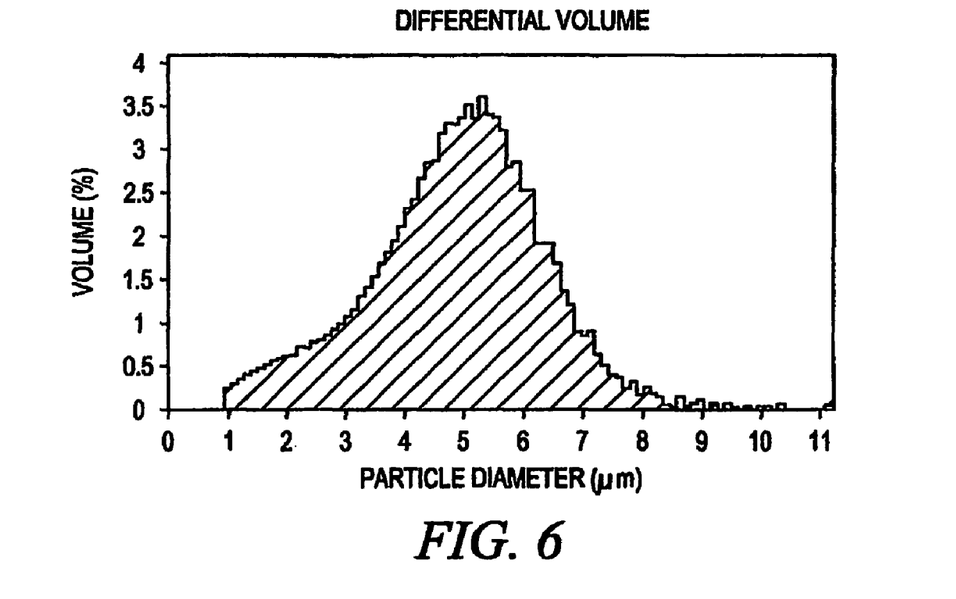
FIG. 6 presents the graph of the size distribution of microparticles of Biotin-PEG-PSA.

Microspheres were prepared using a single emulsion solvent method. 125 mg of PSA-PEG-biotin (15:85) were dissolved in 5 mL of dichloromethane to produce a 25 mg/mL solution. Polyvinyl alcohol (PVA, 250000 Mw) [88% hydrolyzed] was dissolved into distilled water (0.25 g into 250 mL) to make a 0.1% w/v solution. The PSA-PEG-biotin solution was then added to a homogenized PVA solution. The mixture was homogenized for a further 3 minutes at 8000 rpm and then left stirring 3 hours for dichloromethane to evaporate. Particles were collected by centrifugation, washed in distilled water. Micro particle size analysis was performed with a Coulter Multisizer IIe (Beckman-Coulter Inc., Fullerton, Calif.). The microparticles were added to 100 mL of isoton II solution until the coincidence of particles was between 8% and 10%. Greater than 100,000 particles were sized for each batch of microparticles to determine the mean particle size and size distribution (FIG. 6).

Figure 8:
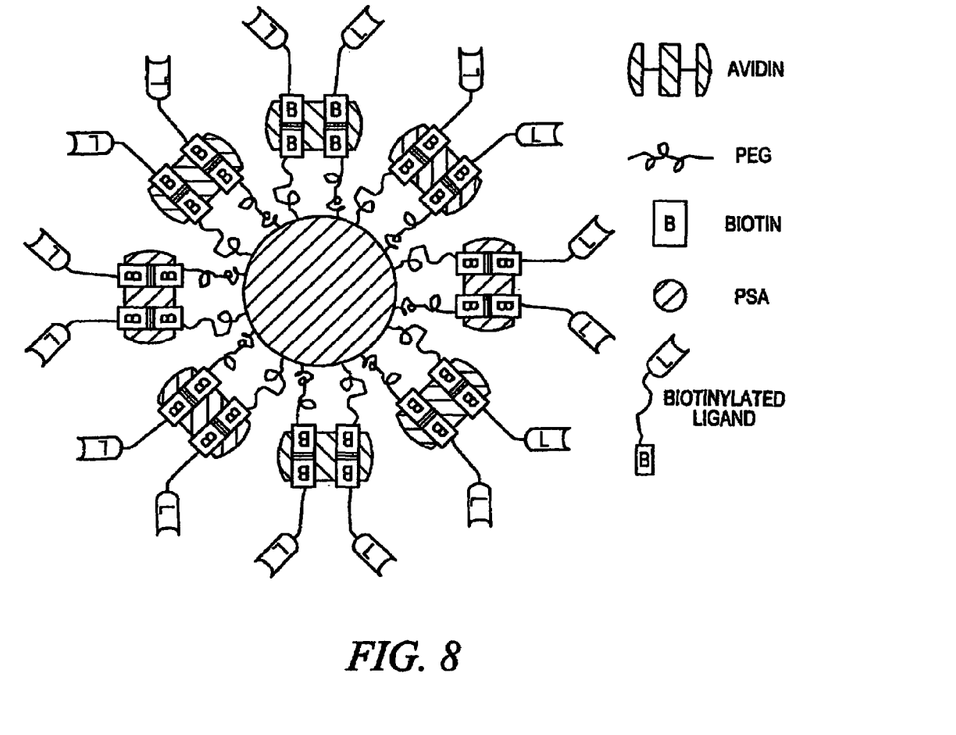
FIG. 8 presents the schematic of a Biotin-PEG-PSA particle that has been modified with a biotinylated ligand.

Microspheres were prepared using a single emulsion solvent method. The phase separation of PEG and PSA upon particle formation ensures that the particle surface is rich in modified (e.g., biotinylated) PEG allowing facile linkage of targeting moieties to the particles at high densities. Texas Red avidin was conjugated to micro and nanosphere and the PSA-PEG particles were then imaged using fluorocene microscopy. Results showed that the Avidin was successfully attached to the particles. Thus, these particle can be further conjugated to desirable biomolecules (e.g., anticancer drug) to provide particles with desired features (see FIG. 8).

REFERENCES

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A block co-polymer, comprising:
   (a) subunits of a diacid; and,
   (b) a subunit of Formula B;

wherein:
   Z is an end group that does not polymerize with the diacid; and,
   n is, independently for each occurrence, an integer from 4-10,000.

2. The polymer of claim 1, wherein the diacid subunits are of formula A:

m is, independently for each occurrence, an integer from 4 to 20; and,
   p is, independently for each occurrence, an integer $\geq 1$.

3. The polymer of claim 2, wherein:
   m is, independently for each occurrence, an integer from 4 to 12; and,
   p is, independently for each occurrence, an integer from 5-10,000.

4. The polymer of claim 2, wherein m is, independently for each occurrence, 8.

5. The polymer of claim 2, wherein Z is Biotin-NH.

6. The polymer of claim 2, wherein the subunits of Formula A comprise between 10% and 99% by weight of the polymer and the subunit of Formula B comprises between 1 and 90% by weight of the polymer.

7. The polymer of claim 6, wherein the subunits of Formula A comprise between 15-98% by weight of the polymer and the subunit of Formula B comprises between 2-60% by weight of the polymer.

8. The polymer of claim 2, having the formula:

9. The polymer of claim 8, wherein the weight ratio of polysebacic acid to PEG-Biotin is selected from 95:5, 85:15, 75:25, and 50:50.

10. The polymer of claim 2, further comprising:
    (c) subunits of a diacid of Formula C:

wherein:
    X is absent or, independently for each occurrence, represents a heteroatom selected from NR, O, and S;
    q is, independently for each occurrence, an integer from 1 to 20; and,
    r is, independently for each occurrence, an integer $\geq 1$.

11. The polymer of claim 10, wherein:
    X is absent at each occurrence;
    q is 3 or 6; and,
    r is, independently for each occurrence, an integer from 5-10,000.

12. The polymer of claim 10, wherein the subunits of Formula A comprise between 10-98% by weight of the polymer, the subunit of Formula B comprises between 1-80% by weight of the polymer, and the subunit of Formula C comprises between 1-95% by weight of the polymer.

13. A pharmaceutical composition, comprising: a polymer of claim 1, wherein the polymer encapsulates an agent selected from: a therapeutic agent, a diagnostic agent, an imaging agent, and an adjuvant.

14. A pharmaceutical composition, comprising: a polymer of claim 1.

15. The pharmaceutical composition of claim 14, wherein the polymer is formulated as microspheres or nanospheres.

16. The pharmaceutical composition of claim 15, wherein the polymer is formulated as microspheres.

17. The pharmaceutical composition of claim 16, wherein the microspheres are suitable for administration by inhalation.

18. An inhaler, comprising: the microspheres of claim 16.

19. A method for treating, preventing, or diagnosing a condition in a patient, comprising: administering to a patient in need thereof a composition of claim 14.

20. The polymer of claim 1, wherein the polymer has a $M_w$ of at least 10,000 daltons.

21. The polymer of claim 20, wherein the polymer has a $M_w$ of at least 25,000 daltons.

22. A composition of claim 1, wherein the subunits of Formula B have a molecular weight of at least 1,000 daltons.

23. A method for preparing a polymer of claim 2, comprising:
(a) combining monomers of Formula $A_1$ and $B_1$; and, $A_1$

$B_1$ (b) reacting the mixture at a temperature and time sufficient to form a polymer, wherein:
$R^1$ is, independently for each occurrence, selected from H;
Y is, independently for each occurrence, selected from H and $C_{1-8}$ alkyl;
Z is a functional group that does not polymerize with the pre-polymer of Formula A;
m is, independently for each occurrence, an integer from 4 to 20;
n is, independently for each occurrence, an integer from 4 to 10,000; and,
p is, independently for each occurrence, an integer $\geq 1$.

24. The method of claim 23, wherein p is, independently for each occurrence, an integer from 5-10,000.

25. The method of claim 23, wherein (a) further comprises: combining monomer of Formula $C_1$ with monomers of Formula $A_1$ and $B_1$;

$C_1$ wherein:
X is absent or, independently for each occurrence, is a heteroatom selected from NR, O, and S;
q is, independently for each occurrence, an integer from 1 to 20; and,
r is, independently for each occurrence, an integer $\geq 1$.

26. The method of claim 25, wherein q is, independently for each occurrence, an integer from 5-10,000.

* * * * *

UNITED STATES PATENT AND TRADEMARK OFFICE
CERTIFICATE OF CORRECTION

| | | |
|---|---|---|
| PATENT NO. | : 8,354,476 B2 | Page 1 of 1 |
| APPLICATION NO. | : 11/721123 | |
| DATED | : January 15, 2013 | |
| INVENTOR(S) | : Justin Hanes et al. | |

It is certified that error appears in the above-identified patent and that said Letters Patent is hereby corrected as shown below:

<u>In the Specification</u>:

At column 8, line 40, please replace "An allyl chains" with --An alkyl chains--;

At column 14, line 39, please replace "confirm" with --confirms--.

Signed and Sealed this
Nineteenth Day of February, 2013

Teresa Stanek Rea
*Acting Director of the United States Patent and Trademark Office*